(12) United States Patent
Jaffe

(10) Patent No.: US 11,807,563 B2
(45) Date of Patent: Nov. 7, 2023

(54) FEAMMOX ACTIVITY IN BIOELECTROCHEMICAL REACTORS

(71) Applicant: The Trustees of Princeton University, Princeton, NJ (US)

(72) Inventor: Peter R. Jaffe, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 155 days.

(21) Appl. No.: 17/280,501

(22) PCT Filed: Sep. 27, 2019

(86) PCT No.: PCT/US2019/053478
§ 371 (c)(1),
(2) Date: Mar. 26, 2021

(87) PCT Pub. No.: WO2020/069327
PCT Pub. Date: Apr. 2, 2020

(65) Prior Publication Data
US 2022/0032349 A1 Feb. 3, 2022

Related U.S. Application Data

(60) Provisional application No. 62/855,208, filed on May 31, 2019, provisional application No. 62/792,971, (Continued)

(51) Int. Cl.
*C02F 3/34* (2023.01)
*B09C 1/10* (2006.01)
(Continued)

(52) U.S. Cl.
CPC ............... *C02F 3/342* (2013.01); *B09C 1/10* (2013.01); *C02F 11/02* (2013.01); *C02F 2101/36* (2013.01)

(58) Field of Classification Search
CPC .. C02F 3/342; C02F 3/346; C02F 3/34; C02F 3/005; C02F 3/305; B09C 1/00; B09C 1/002; B09C 1/10
See application file for complete search history.

(56) References Cited

U.S. PATENT DOCUMENTS 8,932,848 B2 * 1/2015 Cantwell ............... C01B 21/02
423/239.1
8,932,849 B2 * 1/2015 Scherson ............... C01B 21/02
423/239.1
(Continued)

FOREIGN PATENT DOCUMENTS

CN 105271514 A * 1/2016
CN 107098459 A 8/2017
(Continued)

OTHER PUBLICATIONS

International Search Report and Written Opinion corresponding to PCT/US2019/053478, dated Feb. 6, 2020, 11 pages.
(Continued)

*Primary Examiner* — Frederick L Lagman
(74) *Attorney, Agent, or Firm* — J. Clinton Wimbish; Maynard Nexsen PC

(57) ABSTRACT

Microbial reactors are provided for ammonium oxidation. Briefly, a reactor comprises a medium including an ammonium component and a Feammox bacterium and/or enzyme (s) thereof capable of oxidizing ammonium with electron transfer to an anode in contact with the medium. As described further herein, use of the anode as an electron acceptor can mitigate or overcome the disadvantages associated Fe(III) acceptor. In some embodiments, for example, ammonium oxidation in the reactor can proceed in the absence of Fe(III) and/or other metal compounds operable to function as an electron acceptor in the medium. Moreover,
(Continued)

the medium may further comprise one more contaminants in addition to the ammonium component.

16 Claims, 12 Drawing Sheets

Specification includes a Sequence Listing.

Related U.S. Application Data filed on Jan. 16, 2019, provisional application No. 62/737,255, filed on Sep. 27, 2018, provisional application No. 62/737,322, filed on Sep. 27, 2018.

(51) Int. Cl.
*C02F 11/02* (2006.01)
*C02F 101/36* (2006.01)

(56) References Cited

U.S. PATENT DOCUMENTS

| | | | | |
|---|---|---|---|---|
| 9,815,723 B2 * | 11/2017 | Jaffe | | C02F 3/341 |
| 10,479,712 B2 * | 11/2019 | Jaffe | | C02F 3/341 |
| 2015/0321933 A1 * | 11/2015 | Jaffe | | C02F 3/341 |
| | | | | 435/262.5 |
| 2018/0029909 A1 * | 2/2018 | Jaffe | | C02F 3/341 |
| 2020/0277211 A1 * | 9/2020 | Jaffe | | C02F 3/342 |
| 2021/0340042 A1 * | 11/2021 | Jaffe | | B09C 1/10 |

FOREIGN PATENT DOCUMENTS

| | | | |
|---|---|---|---|
| CN | 107555616 A | * | 1/2018 |
| KR | 100193917 B1 | * | 6/1999 |

OTHER PUBLICATIONS

Ruiz-Uriguen et al., Feammox Acidimicrobiaceae bacterium A6, a lithoautotrophic electrode-colonizing bacterium, Authors Manuscript, Apr. 14, 2018 [retrieved on Jan. 9, 2020]. Retrieved from the Internet: <URL:https://www.biorxiv.org/content/10.1101/300731v1.full.pdf>. pp. 1-30.

Kochunarayanan, Biodegradation Potential of Perfluorooctanoate and Perfluorooctane Sulfonate, Thesis Submitted to the Office of Graduate Studies of Texas A&M University, Aug. 2011 [retrieved on Jan. 9, 2020). Retrieved from the Internet: <URL:http://oaktrust.library.tamu.edu/bitstream/handle/1969.1/ETD-TAMU-2011-08-10177/THELAKKAT-KOCHUNARAYANAN-THESIS.pdf?sequence=2&isAllowed=y>, pp. 1-37.

* cited by examiner a.

b.

FEAMMOX ACTIVITY IN BIOELECTROCHEMICAL REACTORS

RELATED APPLICATION DATA

This application is a U.S. National Phase of PCT/US2019/053478, filed Sep. 27, 2019, claims priority pursuant to 35 U.S.C. § 119(e) to U.S. Provisional Application Ser. Nos. 62/737,255 and 62/737,322 filed Sep. 27, 2018, U.S. Provisional Patent Application Ser. No. 62/792,971 filed Jan. 16, 2019, and U.S. Provisional Patent Application Ser. No. 62/855,208 filed May 31, 2019, each of which is incorporated herein by reference in its entirety.

FIELD

The present application relates to systems and methods for environmental remediation and, in particular, to reactors operable for ammonium oxidation via Feammox. The Sequence Listing titled "Sequence Listing," having a file size of 2,867,945 bytes, created on Sep. 29, 2017 and filed herewith is incorporated herein by reference as if fully set forth.

BACKGROUND

Ammonium ($NH_4^+$) is a common compound that can accumulate in soil and water, and it is found in high concentrations in agricultural runoffs and wastewaters as result of its extensive use as fertilizer in crops and because it is a waste product of cellular and animal metabolism. High concentration of $NH_4^+$ can be detrimental for the environment, particularly to water systems. Therefore, nitrification, which is the conversion of $NH_4^+$ to nitrite ($NO_2^-$) and nitrate ($NO_3^-$), is a key step to decrease eutrophication and to lower the demand of dissolved oxygen (DO) in the receiving waters. Low DO puts aquatic biodiversity under pressure, and it is a main cause of general deterioration of ecosystems.

Engineered systems such as wastewater treatment plants (WWTP) or constructed wetlands harness nature's ability to oxidize $NH_4^+$. However, nitrification is energetically intensive as it requires oxygen inputs, which can account for more than 50% of the energy usage in WWTPs invested in the operation of aerators. Therefore, an important goal in wastewater treatment is to oxidize $NH_4^+$ without aeration. Efforts to decrease the oxygen requirements have been done by implementing Anammox in some WWTPs. Anammox oxidizes $NH_4^+$ anaerobically by coupling it to $NO_2^-$ reduction, nonetheless, partial aeration is still required to form the needed $NO_2^-$. Feammox is another $NH_4^+$ oxidation pathway that has the exceptional ability to do it completely under anoxic/anaerobic conditions, thus it does not require aeration like conventional systems, which makes it an attractive candidate for the development of a new form of energy efficient $NH_4^+$ removal. However, it requires iron oxides [Fe(III)] as electron acceptors in a stoichiometric ratio of 6:1, i.e. 6 moles of Fe(III) per 1 mole of $NH_4^+$ oxidized (Equation 1).

$$NH_4^+ + 3Fe_2O_3 \cdot 0.5H_2O + 10H^+ \rightarrow NO^- + 6Fe^{2+} + 8.5H_2O \quad (1)$$

Iron is abundant in the environment and thus Feammox can be enhanced in systems such as constructed wetland as a method to treat some types of wastewater. However, adding Fe(III) to WWTPs is technically inconvenient because iron build-ups are bulky and its removal and disposal is burdensome.

SUMMARY

In view of these disadvantages, microbial reactors are provided for ammonium oxidation. Briefly, a reactor comprises a medium including an ammonium component and a Feammox bacterium and/or enzyme(s) thereof capable of oxidizing ammonium coupled with electron transfer to an anode in contact with the medium. As described further herein, use of the anode as an electron acceptor can mitigate or overcome the disadvantages associated Fe(III) acceptor. In some embodiments, for example, ammonium oxidation in the reactor can proceed in the absence of Fe(III) and/or other metal compounds operable to function as an electron acceptor in the medium. Moreover, the medium may further comprise one more contaminants in addition to the ammonium component.

In another aspect, methods of environmental remediation are described herein. A method of environmental remediation comprises providing a reactor comprising a medium including an ammonium component and a Feammox bacterium and/or enzyme(s) thereof, wherein an anode is in contact with the medium. Ammonium in the medium is oxidized by the Feammox bacterium and/or enzymes thereof coupled with electron transfer to the anode. In some embodiments, the ammonium oxidation proceeds in the absence of Fe(III) and/or other metal compounds operable to function as an electron acceptor in the medium. When present in the medium, other contaminants can also be degraded by the Feammox bacterium and/or enzymes thereof.

These and other embodiments are described further in the following detailed description.

DETAILED DESCRIPTION

Figure 1:
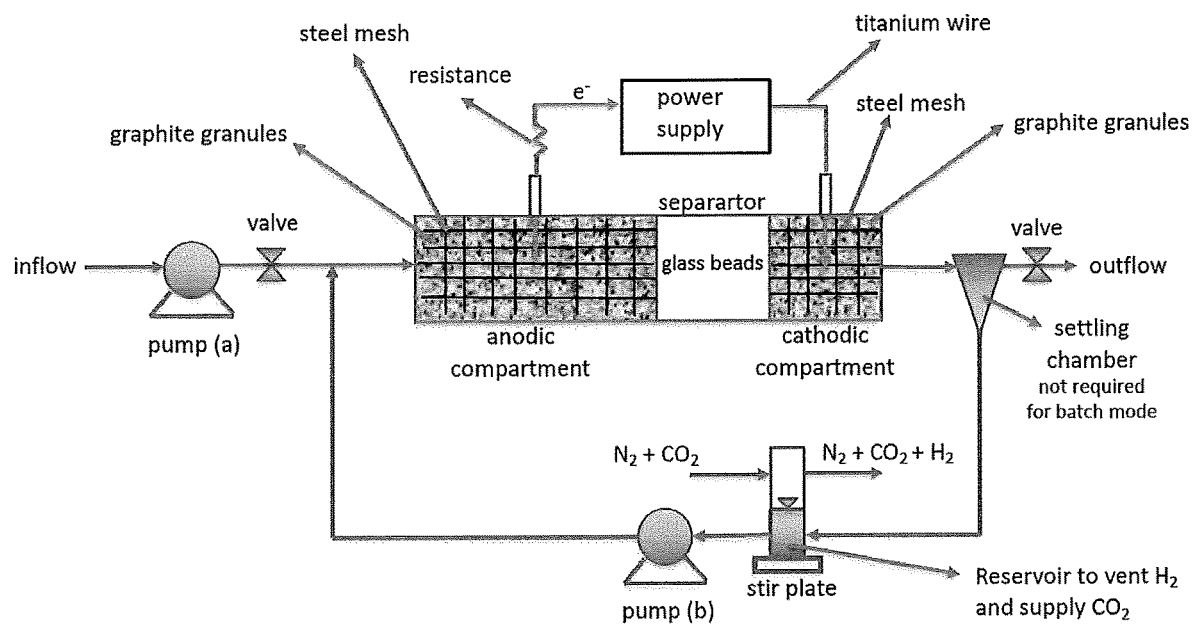
FIG. 1 is a schematic of a reactor according to some embodiments.

Certain terminology is used in the following description for convenience only and is not limiting. The words "right," "left," "top," and "bottom" designate directions in the drawings to which reference is made. The words "a" and "one,"

as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

"Synthetic nucleic acid sequence," "synthetic polynucleotide," "synthetic oligonucleotide," "synthetic DNA," or "synthetic RNA" as used herein refers to a nucleic acid, polynucleotide, oligonucleotide, DNA, or RNA that differs from one found in nature by having a different sequence than one found in nature or a chemical modification not found in nature. The definition of synthetic nucleic acid includes but is not limited to a DNA sequence created using biotechnology tools. Such tools include but are not limited to recombinant DNA technology, chemical synthesis, or directed use of nucleases (so called "genome editing" or "gene optimizing" technologies).

Embodiments described herein can be understood more readily by reference to the following detailed description and examples and their previous and following descriptions. Elements and apparatus described herein, however, are not limited to the specific embodiments presented in the detailed description. It should be recognized that these embodiments are merely illustrative of the principles of the present invention. Numerous modifications and adaptations will be readily apparent to those of skill in the art without departing from the spirit and scope of the invention.

In one aspect, microbial reactors are provided for ammonium oxidation. A reactor comprises a medium including an ammonium component and a Feammox bacterium and/or enzyme(s) thereof capable of oxidizing ammonium coupled with electron transfer to an anode in contact with the medium. In some embodiments, for example, ammonium oxidation in the reactor can proceed in the absence of Fe(III) and/or other metal compounds operable to function as an electron acceptor in the medium.

Turning now to specific components, the medium contained in the reactor comprises an ammonium component. The ammonium component can comprise ammonium and/or compound(s) comprising ammonium. Ammonium containing compounds, for example, can comprise fertilizers, domestic sewage, or industrial effluents. The ammonium component may comprise ammonium chloride and/or any other ammonium salt. The ammonium component may also be a nitrogen containing organic compound, wherein nitrogen may be hydrolyzed to ammonium.

The medium also comprises a Feammox bacterium and/or enzyme(s) thereof capable of fluorochemical degradation in conjunction with oxidation of ammonium and electron transfer to the electron acceptor, such as the anode. The Feammox bacterium may be an Actinobacterium or a bacterium with a similar genetic composition. In some embodiments, for example, the Feammox bacterium is an *Acidimicrobiaceae* bacterium or variant thereof. The Feammox bacterium may be a bacterial strain that was isolated from wetland soils collected in New Jersey after a series of enrichment incubations. The soil samples were collected at the location identified as 40° 15' N–74° 30' W or within 100 m of the identified location. The Feammox bacterium may be the bacterial strain designated the *Acidimicrobiaceae* Feammox bacterium A6 or variant thereof. In being a variant in some embodiments, the bacterium may have at least 70% genome overlap with an Actinobacterium. The *Acidimicrobiaceae* Feammox bacterium A6 was submitted for deposit with the American Type Culture Collection (ATCC; 10801 University Blvd. Manassas, Va. 20110-2209, USA) on Apr. 27, 2015, the submission was supplemented on May 7, 2015, and was assigned Accession Deposit Number PTA-122488 on Sep. 17, 2015. The *Acidimicrobiaceae* Feammox bacterium may have a genome comprising, consisting essentially of, or consisting of a nucleic acid sequence with at least 70, 72, 75, 80, 85, 90, 91, 92, 93, 94, 95, 96, 97, 98, 99, or 100% identity to SEQ ID NO: 1. The Feammox bacterium may have the genome size of 3.3 mega base pairs (Mb) and guanine-cytosine content 52%. The bacterial genome may further include a gene encoding a Feammox Ammonium Monooxygenase. As used herein, the term "Feammox Ammonium Monooxygenase" (FMO) refers to an enzyme that plays a key role in oxidizing ammonium coupled with ferric iron reduction. The FMO also refers to genes encoding clones or different variants of the Feammox Ammonium Monooxygenase. The gene may include a nucleic acid comprising, consisting essentially of, or consisting of a nucleic acid sequence with at least 70, 72, 75, 80, 85, 90, 91, 92, 93, 94, 95, 96, 97, 98, 99, or 100% identity to a sequence selected from the group consisting of: SEQ ID NOS: 8-28. The Feammox Ammonium Monooxygenase may include an amino acid comprising, consisting essentially of, or consisting of a nucleic acid sequence with at least 70, 72, 75, 80, 85, 90, 91, 92, 93, 94, 95, 96, 97, 98, 99, or 100% identity to a sequence selected from the group consisting of: SEQ ID NOS: 29-49. The Feammox bacterium may be live or lyophilized.

| SEQ ID NOS of FMO Related Enzymes and Genes | | |
|---|---|---|
| FMO clone* | SEQ ID NO (Gene) | SEQ ID NO (Enzyme) |
| ERCFMO_0001 | 8 | 29 |
| ERCFMO_0002 | 9 | 30 |
| ERCFMO_0003 | 10 | 31 |
| ERCFMO_0004 | 11 | 32 |
| ERCFMO_0005 | 12 | 33 |
| ERCFMO_0006 | 13 | 34 |
| ERCFMO_0007 | 14 | 35 |
| ERCFMO_0008 | 15 | 36 |
| ERCFMO_0009 | 16 | 37 |
| ERCFMO_0010 | 17 | 38 |
| ERCFMO_0011 | 18 | 39 |
| ERCFMO_0012 | 19 | 40 |
| ERCFMO_0013 | 20 | 41 |
| ERCFMO_0014 | 21 | 42 |
| ERCFMO_0015 | 22 | 43 |
| ERCFMO_0016 | 23 | 44 |
| ERCFMO_0017 | 24 | 45 |
| ERCFMO_0018 | 25 | 46 |
| ERCFMO_0019 | 26 | 47 |
| ERCFMO_0020 | 27 | 48 |
| ERCFMO_0021 | 28 | 49 |

In some embodiments, Feammox bacteria and related enzymes are described in U.S. Pat. No. 9,815,723 which is incorporated herein by reference in its entirety.

Determining percent identity of two nucleic acid sequences may include aligning and comparing the nucleotides at corresponding positions in the two sequences. If all positions in two sequences are occupied by identical nucleotides then the sequences are said to be 100% identical. Percent identity may be measured by the Smith Waterman algorithm (Smith T F, Waterman M S 1981 "Identification of Common Molecular Subsequences," *J Mol Biol* 147: 195-197, which is incorporated herein by reference as if fully set forth).

As described herein, the medium may comprise one or more enzymes, such as FMO, in addition to the Feammox bacterium for the oxidation of ammonium coupled with electron transfer to the electron acceptor. Alternatively, one or more enzymes, such as FMO, can be present in the medium in the absence of the Feammox bacterium. In such embodiments, the one or more enzymes can be responsible for ammonium oxidation and electron transfer. In some embodiments, for example, FMO is isolated from Feammox bacterium and employed in the medium. In other embodiments, the one or more enzymes may be fabricated via synthetic chemical techniques.

The reactor also comprises an anode in contact with the medium. The anode can serve an as electron acceptor in the ammonium oxidation process. By serving as an electron acceptor, the anode can partially or completely replace one or more metals in the medium that function as an electron acceptor in the ammonium oxidation process. For example, the anode can partially or fully replace Fe(III) in the medium. Accordingly, the ammonium oxidation reaction involving the Feammox bacterium and/or enzyme(s) thereof can proceed in the absence of iron, thereby mitigating or overcoming disadvantages of prior processes requiring the presence of iron and/or other metal. The anode can be constructed of any material(s) consistent with the ammonium oxidation processes described herein. In some embodiments, the anode comprises metal or alloy. Alternatively, the anode can be constructed of an electrically conductive non-metallic material. For example, the anode can comprise electrically conductive carbon. In some embodiments, the electrically conductive carbon comprises graphite. The anode may also exhibit various morphologies. The anode, in some embodiments, may be monolithic in nature. Alternatively, the anode may be particulate. Graphite particles, for example, can form all or part of the anode. In some embodiments, a metal or alloy cage can contain the particulate material and form part of the anode. Particulate material of the anode can have particle size, surface area, packing characteristics and/or porosity advantageous for contacting or otherwise interacting with the medium. The Feammox bacterium can colonize the anode, in some embodiments. In such embodiments, the Feammox bacterium can transfer electrons directly to the anode. Electron transfer to the anode can result from oxidation of the ammonium in the medium.

The reactor, in some embodiments, comprises an anodic compartment in which the medium is disposed. The anodic compartment, for example, can be filled with anodic material, such as graphite. In some embodiments, metal or alloy mesh can be employed with the anodic material to reduce electrical resistivity of the anodic compartment. Metal or alloy mesh can be particularly useful when the anodic material is particulate and/or an electrically conductive non-metallic material. When in liquid form, the medium may be passed over and/or through the anodic compartment. The reactor may also comprise a cathode or cathodic compartment. The cathode or cathodic compartment can be separated from the anode or anodic compartment by a separator. The separator can comprise any electrically insulating material. In some embodiments, for example, the separator is glass. The glass separator may be provided in particulate or bead form to permit flow of the medium from the anodic compartment to the cathodic compartment. FIG. 1 is a schematic of a reactor according to some embodiments.

In some embodiments, a potential can be applied to the anode and cathode of the reactor. In other embodiments, no potential is applied to the anode and cathode, and the electron transfer process occurs under natural redox potential gradients. In some embodiments, the anode and cathode can be placed directly in a contaminated environment, such as soil, sediments, and/or wetlands, and methods described herein occur under natural redox potential gradients. The anode and cathode, for example, can be placed in different zones of the medium in the natural habitat to effectuate methods described herein. Accordingly, methods described herein can be practiced in situ of contaminated environment and/or within compartments of a constructed reactor.

The reactor may be a continuous reactor or a batch reactor. In an embodiment, a reactor may be an industrial-type reactor. The reactor may operate within a water treatment plant. The reactor may be a treatment pond or a reservoir. The reactor may be a tank for wastewater storage.

Reactor conditions may generally include a temperature in a range from 4° C. to 35° C. The temperature may be in a range between any two integer value temperatures selected from 4° C. to 35° C. The temperature may be in a range between and including 4° C. to 10° C., 10° C. to 15° C., 15° C. to 20° C., 20° C. and 25° C., 25° C. and 30° C., 30° C. and 35° C. The temperature may be any one integer value temperature selected from those including and between 4° C. and 35° C. or 15° C. to 35° C. Temperatures between room temperature and 40° C. may be used. The temperature may be any one temperature including and between room temperature and 35° C. Temperatures between 20° C. and 35° C. may be used. The temperature may be any temperature including and between 20° C. and 25° C.

The reactor may be operated for any desired time period. In some embodiments, the reactor is operated for a time period ranging from 2 hours to 45 days. The time period may be 5 hours, 10 hours, 15 hours, 20 hours, 1 day, 2 days, 3 days, 4 days, 5 days, 10 days, 15 days, 20 days, 25 days, 30 days, 35 days, 40 days or 45 days. The time period may be any one integer value selected from those including and between value points, endpoints inclusive. The time period may be greater than 45 days. The time period may be less than 1 day. In continuous flow reactors or in batches, the process may last from several hours to several months. For continuous flow reactors, the time period may depend on the bacterial concentration in the inoculum. Higher bacterial concentration in the inoculum may result in a shorter remediation time. The time period may depend on hydraulic retention capacity of a continuous flow reactor. Lower retention capacity of the continuous flow reactor may result in a shorter remediation time. Hydraulic residence time for the continuous flow reactors may be from 3 hours to 4 hours, from 3 hours to 5 hours, from 3 hours to 6 hours, from 3 hours to 7 hours, from 3 hours to 8 hours, from 3 hours to 10 hours, from 3 hours to 15 hours, from 3 hours to 20 hours, from 3 hours to 1 day, from 3 hours to 2 days, from 3 hours to one or several weeks. Hydraulic residence time may be any integer value selected from those including and between value points, endpoints inclusive.

pH of the medium in the reaction can range from 2.0 to 9.0. The pH of the medium may be in a range between and including 2.0 and 3.0, 3.0 and 4.0, 4.0 and 5.0, 5.0 and 6.0, 6.0 to 7.0, 7.0 to 7.5. The pH may be any one integer value pH selected from those including and between 2.0 and 7.5. The pH may be any pH including and between 4.0 and 7.0.

Figure 2:
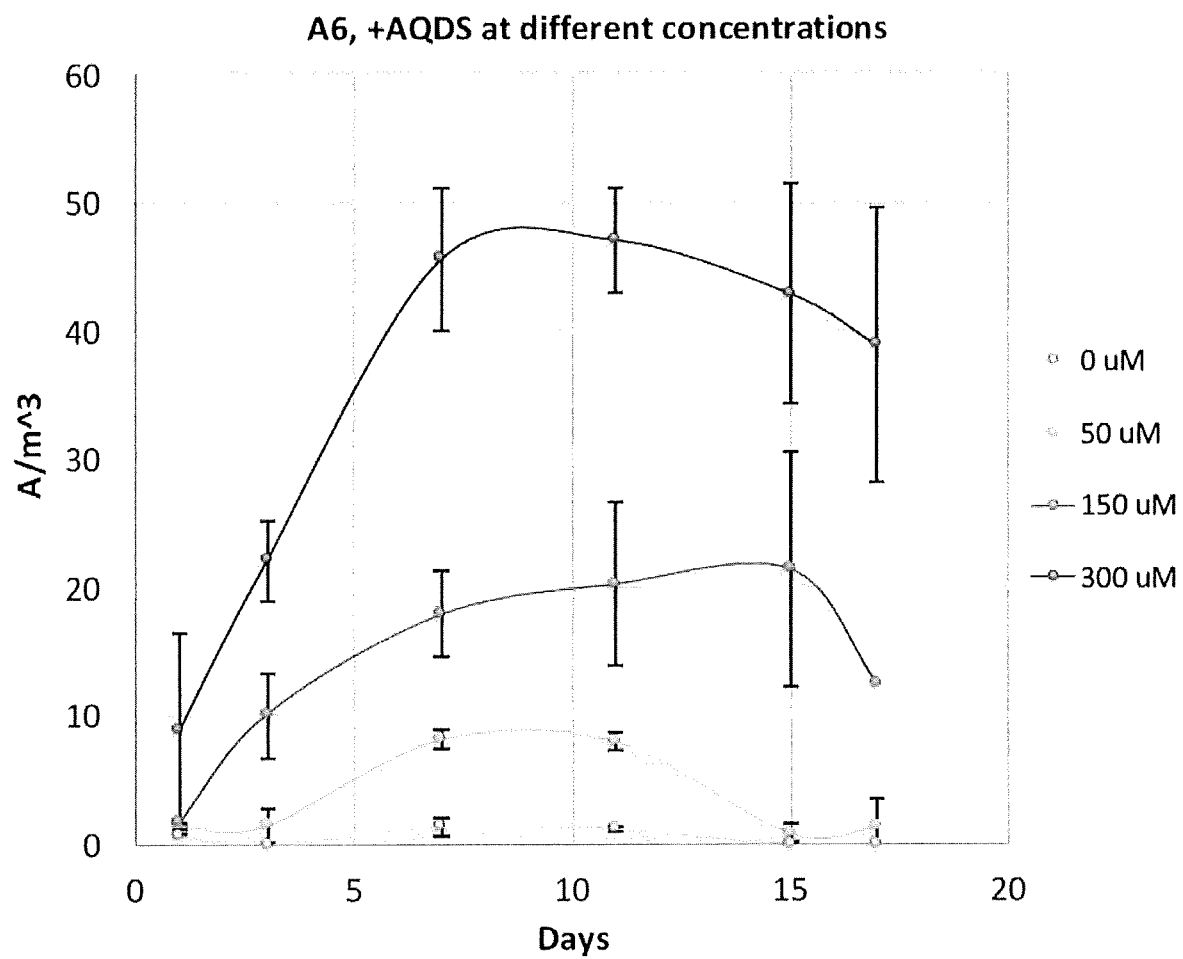
FIG. 2 illustrates current density of a reactor relative to AQDS concentration according to some embodiments.

In some embodiments, the medium further comprises one or more electron shuttling compounds. Any electron shuttling compound consistent with the objectives of ammonium degradation can be used. In some embodiments, an electron shuttling compound is 9,10-Anthraquinone-2,7-disulphonic acid (AQDS). As discussed further herein, the electron shuttling compound can enhance the ammonium oxidation process and/or degradation of other contaminant species in the medium. Presence of the electron shuttling compound can result in higher current densities produced by the reactor. FIG. 2 illustrates current density of a reactor relative to AQDS concentration according to some embodiments. The electron shuttling compound can be present in the medium in any desired amount. In some embodiments, the electron shuttling compound is present in an amount of 10 μg/l to 1 mg/l. In some embodiments, an electron shuttling compound, such as AQDS, can serve as the electron acceptor, thereby permitting the oxidation of ammonium to proceed in the absence of the anode and/or other electron acceptor.

The medium, in some embodiments, further comprises one or more chemical species operable to inhibit or preclude accumulation of nitrite ($NO_2^-$) in the medium. Accumulation of nitrite can retard Feammox processes. Therefore, removal of nitrite from the medium can assist in efficient functioning of the reactor. The medium, for example, can include a denitrifier and suitable electron donor, such as organic carbon or elemental sulfur, to effectuate nitrite removal. Additionally, $CO_2$ is added to the medium, in some embodiments. Presence of $H_2$ in the medium can result in the Feammox bacterium consuming $H_2$ instead of ammonium. Accordingly, $CO_2$ is added to the medium and/or atmosphere surrounding the medium to remove $H_2$ and to provide a carbon source. In some embodiments, for example, $CO_2$ is added via a $N_2$:$CO_2$ flush of the medium and surrounding environment. $N_2$ and $CO_2$ can be present in any desired ratio. In some embodiments, $CO_2$ can be derived from other chemical species, such as bicarbonate. Additions of bicarbonate to the medium may require pH adjustment to the medium. Notably, degradation of organic compounds in the Feammox process can also produce $CO_2$. In such embodiments, $CO_2$ addition(s) to the medium may not be required. In some embodiments, $CO_2$ can be derived from the degradation of organic compounds.

The medium can further comprise one or more contaminants in addition to the ammonium component. In some embodiments, the one or more contaminants are selected from the group consisting of fluorochemicals, chlorinated volatile organic compounds, perchloroethylene (PCE), trichloroethylene (TCE), trichloroethane, dichloroethane, vinyl chloride, polychlorinated biphenyls, fuel constituents, benzene, ethylbenzene, toluene, xylene, phenanthrene, methyl tert butyl ether, tertiary butyl alcohol, polyaromatic hydrocarbons, and ethylene dibromide. One or more fluorochemicals selected from the group consisting of perfluoroalkyl compounds, polyfluoroalkyl compounds, fluorinated carboxylic acids, fluorinated alcohols, and fluorinated sulfonates. In some embodiments, the fluorochemical component comprises one or more compounds selected from Table I.

TABLE I

| Fluorochemicals |
| --- |
| Heptafluorobutyric acid (HFBA) |
| Perfluorooctanoic acid (PFOA) |
| 2,2,2-Trifluoroethyl Nonafluorobutanesulfonate (PFBS) |
| 6:2 Fluorotelomer sulfonate (6:2 FTS) |
| 8:2 Fluorotelomer Alcohol (8:2 FTOH) |
| Ammonium 4,8-dioxa-3H-perfluorononanoate (ADONA) |
| Perfluorobutanoic acid (PFBA) |
| Perfluorooctane sulfonamide (FOSA) |

TABLE I-continued

| Fluorochemicals |
| --- |
| Perfluorooctane sulfonate (PFOS) |
| Perfluoroheptane sulfonate (PFHpS) |
| Perfluorohexane sulfonate (PFHxS) |
| Perfluoropentanoic acid (PFHeA) |
| Perfluoroheptanoic acid (PFHpA) |
| Perfluorohexanoic acid (PFHxA) |
| Perfluoropentane sulfonate (PFPeS) |
| Pentafluoropropionic acid (PFPrA) |
| 6:2 Fluorotelomer alcohol (6:2 FTOH) |
| 8:2 Fluorotelomer phosphate diester (8:2 diPAP) |
| 8:2 Fluorotelomer sulfonate (8:2 FTS) |

Contaminant in addition to the ammonium component may also comprise one or more inorganic compounds. In some embodiments, an inorganic contaminant comprises uranium and/or selenium. Uranium and selenium, for example, are reduced via the Feammox process.

The medium can comprise water, soil or mixtures thereof. The water can be any source of water, including ground water, lakes, streams and/or reservoirs. In some embodiments, the water is wastewater. As used herein, the term "wastewater" refers to any water that has been adversely affected in quality by anthropogenic influence. Wastewater may be municipal wastewater, industrial wastewater, agricultural wastewater, surface runoff, landfill leachate, stormwater, or wastewater combining wastewater from multiple sources. Wastewater may be treated in a wastewater treatment plant. Similarly, soil may be any soil that has been adversely affected in quality by anthropogenic influence. The soil may include groundwater. The groundwater may comprise wastewater described herein.

In some embodiments, the medium may further comprise a carrier. The carrier may support growth of the Feammox bacterium. The carrier may comprise a filter, beads, agarized medium, or any surface that allows bacterial attachment. The carrier may include media for culturing the Feammox bacterium. The media may be inorganic $NH_4^+$-ferric iron media. The inorganic $NH_4^+$-ferric iron media may be solid media or liquid media. The liquid media may include but not limited to the following components: $NH_4Cl$, $(NH_4)_2SO_4$, $NaHCO_3$, $KHCO_3$, $KH_2PO4$, 100 mg $MgSO_4·7H_2O$, and $CaCl_2·2H_2O$. The liquid media may further include ferrihydrite, AQDS, trace element solution or vitamins Vitamins may be but are not limited to ATCC® vitamins. The liquid media may have a pH in a range from 4.0 to 5.0. The media may include traces of dissolved oxygen. The solid medium may have the same composition as the liquid media but include elements to solidify the mixture. The solid media may be solidified with 0.8% agar. The solid media may include ferrihydrite that is spread on the surface of the medium.

In another aspect, methods of environmental remediation are described herein. A method of environmental remediation comprises providing a reactor comprising a medium including an ammonium component and a Feammox bacterium and/or enzyme(s) thereof, wherein an anode is in contact with the medium. Ammonium in the medium is oxidized by the Feammox bacterium and/or enzymes thereof coupled with electron transfer to the anode. In some embodiments, the ammonium oxidation proceeds in the absence of Fe(III) and/or other metal compounds operable to function as an electron acceptor in the medium. When present in the medium, other contaminants can also be degraded by the Feammox bacterium and/or enzymes thereof.

Components of the medium, including the ammonium component, fluorochemical component, anode and Feammox bacterium and/or enzyme(s) thereof can have any properties and/or compositions described hereinabove. Moreover, the medium can comprise water, soil, sludge, sorbent porous materials, and/or any solid contaminated with the pollutants described herein. Water of the system can be any source of water, including wastewater, ground water, lakes, streams and/or reservoirs.

These and other embodiments are further illustrated by the following non-limiting examples.

Example 1—Feammox Reactor Employing Electrodes

Figure 3:
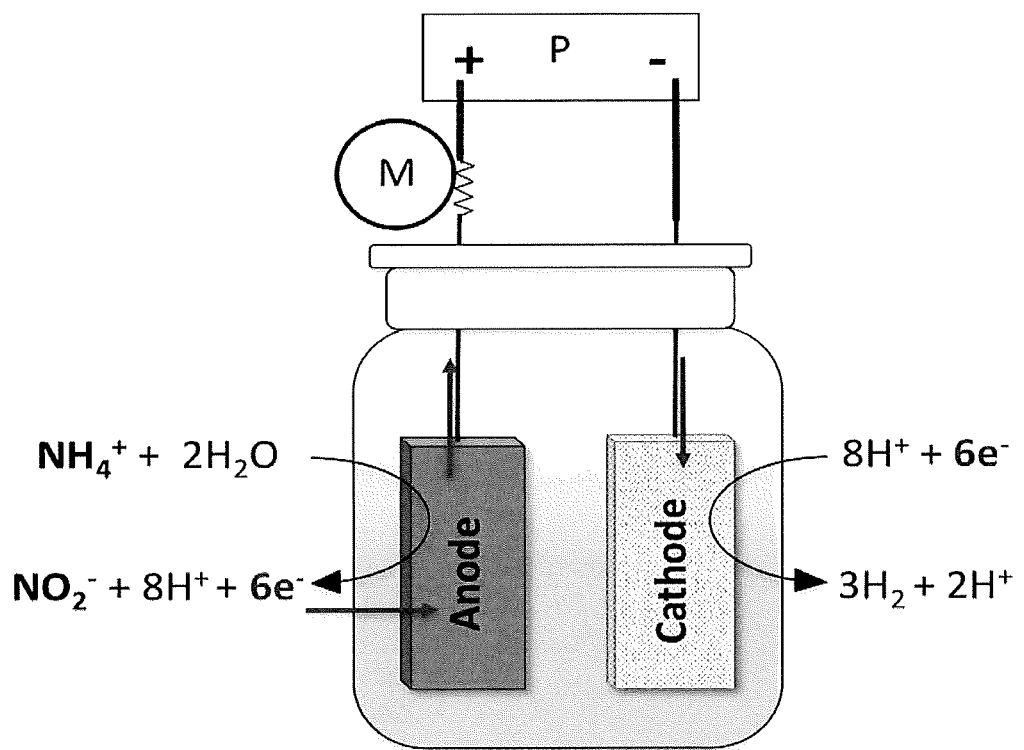
FIG. 3 is a schematic of a biotic Feammox-MEC according to some embodiments.
Figure 4:
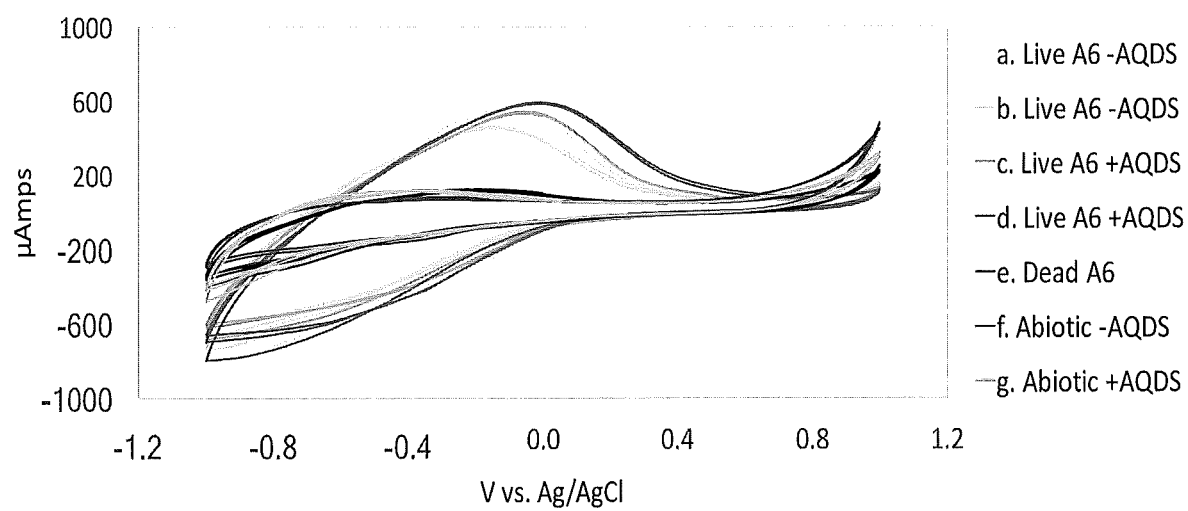
FIG. 4 are cyclic voltammetry scans for Feammox-MECs with and without Feammox bacterium and with and without electron shuttling compound according to some embodiments.

Cyclic voltammetry (CV) was performed on biotic Feammox-MECs in order to determine the optimal applied potential ($V_{app}$) for electron transfer process to the anode. FIG. 3 is a schematic of the Feammox MEC used in this Example. CV was also performed using MECs with dead (autoclaved) bacteria, and on blank abiotic controls. Each CV for the biotic and blank abiotic controls was performed with and without AQDS to determine if the added electron shuttle had any additional effect on the $V_{app}$. Results (FIG. 4) show that the optimal $V_{app}$ for all biotic Feammox-MECs containing AQDS was $-0.03\pm0.025$ V vs. Ag/AgCl (3.5 M KCl, +205 mV vs the standard hydrogen electrode, SHE), while for the experiments without AQDS the optimal $V_{app}$ was shifted slightly toward more negative values, $-0.11\pm0.035$ V vs. Ag/AgCl. Using these optimal $V_{app}$ to calculate the $\Delta G°$ for the reactions, using Nernst equation, results in $-59.77$ kJ/mol for the biotic reactors with AQDS, and $-15.34$ kJ/mol for the biotic reactors without AQDS.

Other studies on $NH_4^+$ removal using bioelectrochemical systems inoculated with sludge from wastewater treatment plants reported current oxidation peaks of 0.59 V vs Ag/AgCl and 0.53 V vs Ag/AgCl. The conditions used in those studies, such as pH of 7.7 (Feammox reaction requires acidic pH), and the associated microbial community, are different from the ones presented here. Therefore, the anaerobic $NH_4^+$ removal reported by those studies does not appear to be associated to the Feammox reaction. Similar oxidation peaks ($-0.08$ vs. Ag/AgCl) to the ones found for the Feammox-MECs have been reported for other bioelectrogenic system, but it is unknown to what type of exocelullar or extracellular electron transfer compounds it is associated with.

The CV on abiotic and dead controls did not show a peak near the oxidation peak for the biotic reactors. The controls showed a current peak at 1.00 V which is thought to be due to hydrogen evolution, a common electrochemical process in abiotic and biotic systems. Hydrogen evolution results from the hydrolysis of water, which takes place starting at 0.82 V. The amplitude of the voltagram on the reverse scans is believed to be due to a pseudocapacitance behavior of the system. Protons ($H^+$) adsorb to the surface of the electrode prior to hydrogen evolution, and desorb during the reverse scan if $H_2$ was not produced. The proposed $NH_4^+$ oxidation reaction in the Feammox-MECs ($NH_4^+ + H_2O \rightarrow NO_2^- + 3H_2 + 2H^+$) (FIG. 3) supports the increased amplitude of the voltagram during reverse scanning, because not all protons are converted to $H_2$, thus they undergo adsorption and desorption during scans.

Feammox-MECs with Enriched *Acidimicrobiaceae* sp. A6 Culture

Figure 5:
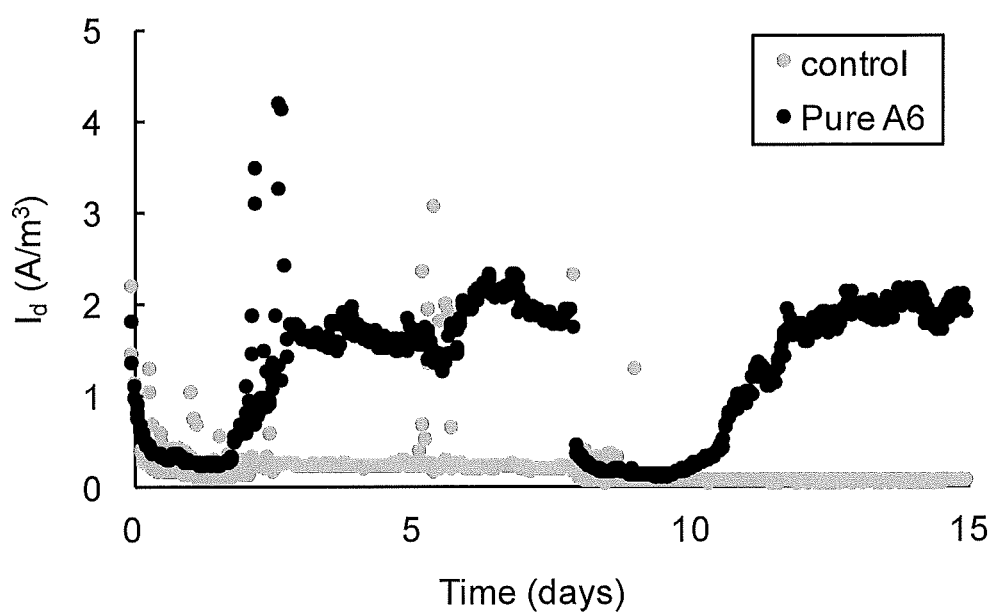
FIG. 5 is the illustrated the average current density in MECs containing enriched A6 culture according to some embodiments.

Our results showed that A6 has the ability to be active in MECs, under constant mixing and with a $V_{app}$. MECs seeded with an enriched A6 culture containing $NH_4^+$ produced an average current density ($I_d$) of 2.5 A/m³ (FIG. 5), and removed a total of 0.52 mM $NH_4^+$ after 3 weeks of operation, however current production lasted for 2 weeks before the system became unstable because the connection between electrodes and wires became loose due to the constant movement of the shaker plate. Control conditions showed negligible $I_d$ and no change in $NH_4^+$ concentration.

Microbial Community Composition Analysis

Figure 6:
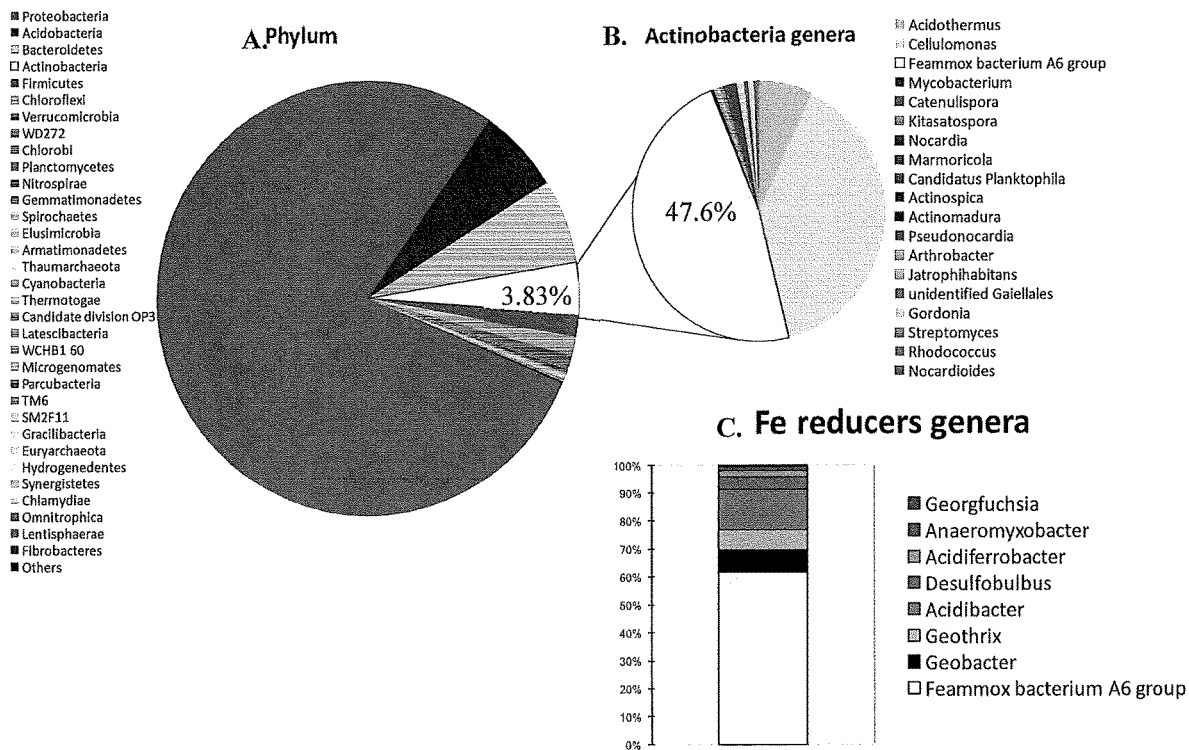
FIG. 6 illustrates microbial community composition from a Feammox-MEC according to some embodiments.

The microbial community of a working Feammox-MEC culture (FIG. 6) was composed of 3.83% Actinobacteria phylum, of which 47.6% was classified at the genus level as Feammox bacterium A6, i.e. *Acidimicrobiaceae* sp. A6. Feammox bacterium A6 makes up 61.6% of the total diversity of all other Fe-reducing bacteria (ERB) present in the culture. Other present ERB that are also known to be electrogenic bacteria that can power bioelectrochemical systems include *Geobacter* (7.8%), *Geothrix* (7.2%), and *Desulfobulbus* (4.7%), however, they require organic C as their electron source and this was not provided at all in the system. The only source of C was $CO_2$ because A6 is an autotroph, therefore, we attribute the presence of other ERB to be remnants of the initial microbial community as well as biomass turnover. The only electron source available in the system was $NH_4^+$.

There are a very limited number of studies on bioelectrochemical $NH_4^+$ oxidation using electrodes as the electron acceptor, and they conclude that the key organism responsible for this process is Nitrosomas (Proteobacteria), a group not found in the Feammox-MECs cultures. Nitrosomas are common aerobic nitrifiers present in soil, freshwater and wastewater. A6 is an Fe reducer that carries out Feammox, the only fully anaerobic $NH_4^+$ oxidation process known, hence, we attribute the current production and ammonium oxidation in the MECs to A6 activity. No current was observed in the control MECs with dead A6, abiotic MECs nor in the MEC operated with live A6 but without $NH_4^+$.

Feammox-MECs with Pure *Acidimicrobiaceae* sp. A6 Culture

Figure 7:
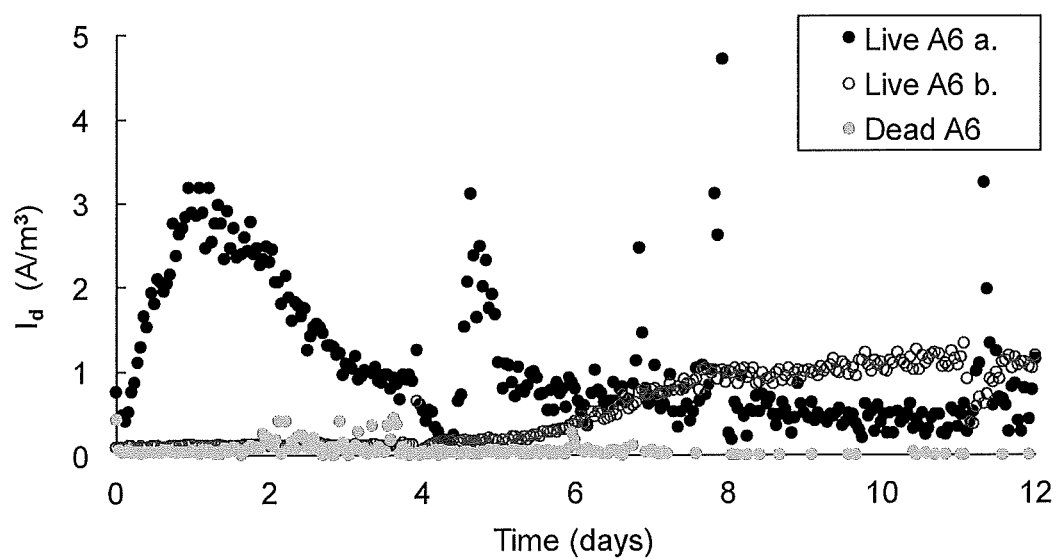
FIG. 7 illustrates average current density measure in 2 MEC replicas containing pure A6 culture.

Replicas of the MECs run with pure A6 culture had $I_d$ peak at different time points. For example, live A6 culture (a) peaked on day one with a maximum $I_d$ of up to 3.2 A/m³, while live A6 culture (b) only ramped up on day 5 but never peaked, instead it showed a stable increase on $I_d$ and then leveled out (FIG. 7, for other replicas of MECs with live A6 see supplemental material Figure S1). All control conditions, including MECs with dead A6, abiotic MECs and MECs with live A6 without $NH_4^+$ showed negligible $I_d$. Although MECs were operated for 3 weeks, $I_d$ data is shown only for a 2-weeks period, because after that the connections to the electrodes became loose due to the constant shaking, resulting in noisy data resulted.

Figure 8:
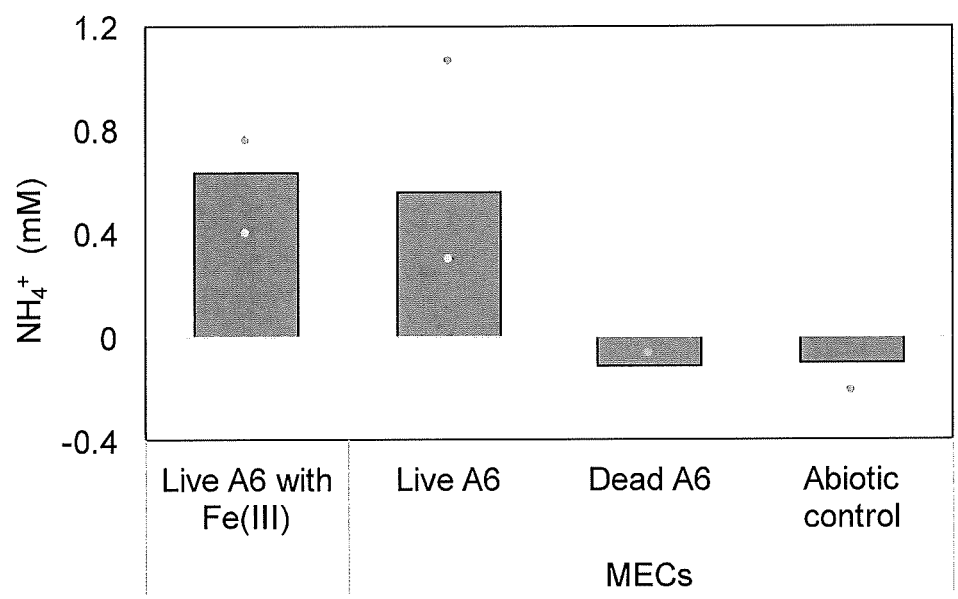
FIG. 8 illustrates average $NH_4^+$ removal from MECs employing media of various composition according to some embodiments.

All MECs containing live A6 removed on average $0.6\pm0.25$ mM of $NH_4^+$, which is similar to the amount removed for cultures grown using Fe(III) as the electron acceptor over the same time period, i.e. $0.6\pm0.14$ mM of $NH_4^+$. The control conditions showed no removal of $NH_4^+$, instead a slight increase in $NH_4^+$ concentration was detected ($+0.11\pm0.09$ mM of $NH_4^+$) (FIG. 8), which is attributed to decaying biomass. Quantification of biomass from MECs with pure live A6 showed that its biomass can be sustained as good as when A6 is cultured with Fe(III) as the electron acceptor over 3 weeks of operation ($2.90\times10^9$ copies of DNA/ml in MECs and $3.35\times10^9$ copies of DNA/ml in batch culture with Fe(III)).

Mixing of the medium in the MECs in necessary to facilitate electron diffusion from the cells to the electrode.

Figure 9:
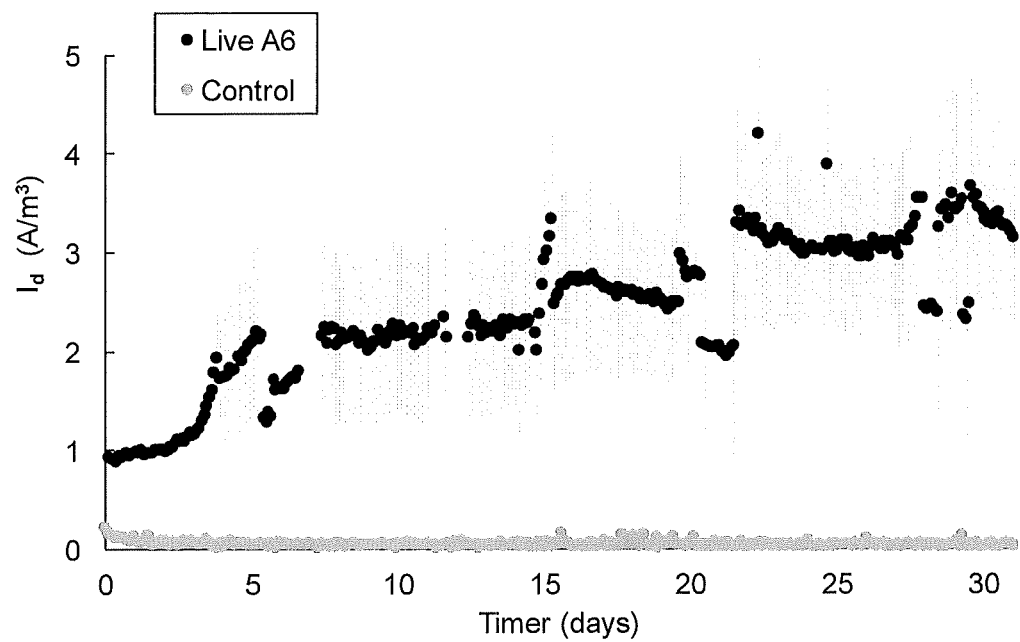
FIG. 9 illustrates average current density of MECs with pure A6 under stirring conditions according to some embodiments.

However, using a shaker for this purpose did result in deterioration of the connections in the MECs. Therefore, to expand the operational time of the MECs, we tested the use of magnetic stirring bars in each reactor, which where placed on a stirring plate. This change resulted in MECs with pure A6 culture to be capable of operating for over 1 month, with continuous increase in $I_d$ over time (FIG. 9). MECs removed an average of 0.7±0.03 mM of $NH_4^+$, comparable to the bench pure A6 cultures containing Fe(III) which removed 0.64 mM of $NH_4^+$. Both, MECs and bench cultures sustained similar amount of A6 biomass ($2.11 \times 10^9$ copies of DNA/ml in MECs and $6.97 \times 10^9$ copies of DNA/mi in batch culture with Fe(III)).

Figure 10:
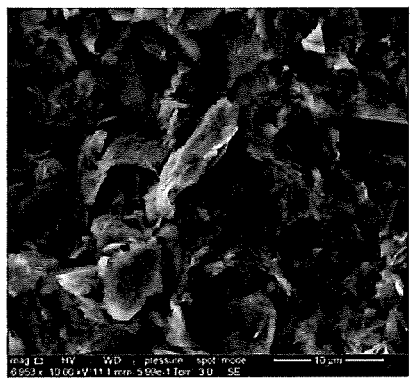
FIG. 10 are scanning electron microscopy images of (a) the graphite anode of a control MEC operated with dead A6 and (b) the graphite anode of a MEC operated with live A6.
Figure 10:
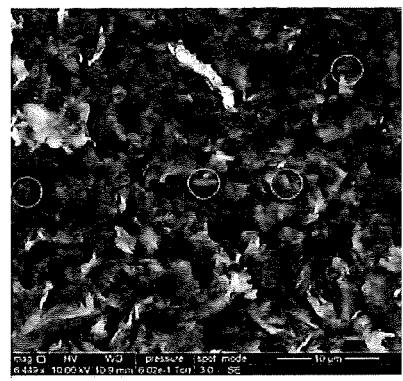

Additionally, the anode of one of the MECs operated with live A6 and the anode of one of MECs containing dead A6 were analyzed through scanning electron microscopy, bacteria cells attached to the surface of the anode of the MEC with life bacteria were observed, while in the control MECs with dead bacteria, no cells could be found on the electrode's surface (FIG. 10).

CONCLUSIONS

This study shows that MECs seeded with enrichment and pure culture of the Feammox bacteria *Acidimicrobiaceae* sp. A6 can carry out anaerobic $NH_4^+$ oxidation while using the anode as the electron acceptor. Cyclic voltammetry shows oxidation peaks of −0.03±0.025 V vs. Ag/AgCl for MECs with AQDS, and −0.11±0.035 V vs. Ag/AgCl for MECs without AQDS, thus confirming that confirming that the reaction is thermodynamically feasible.

Current density of up to 3.2 Amps/m$^3$ were measured in MECs within 2 weeks, and up to 4.2 Amps/m$^3$ were measured in MECs that operated for over 1 month. $CO_2$ was thought to be a limiting factor. It is contemplated to set up a 2-chamber MEC, where the production of $H_2$ does not go in contact with A6, as is has been shown that A6 has the ability to use hydrogen as its energy source.

Materials and Methods
Experimental Setup

MECs were constructed and run in parallel as described by Call and Logan (2011) (FIG. 2). The MECs were built in a 10 ml glass serum bottle containing a graphite plate as the anode [1.5 (H)×1 (L)×0.32 cm (W)] (Grade GM-10; GraphiteStore.com Inc.), and stainless steel (SS) mesh as the cathode [1.5 (H)×1 (L) cm] (Corrosion-resistant 304 Stainless Steel woven wire cloth, 90×90 mesh, 0.0055" wire diameter). Each graphite electrode set was connected by a 5 cm long titanium (Ti) wire (ultra-corrosion-resistant Ti wire, 0.08 cm in diameter, McMaster-Carr code 90455k32), and each SS cathode to a 5 cm long SS wire (302/304 Stainless Steel wire, 0.032" diameter, McMaster-Carr code 85385T99). The headspace of each MEC was purged with an 80% $N_2$, 20% $CO_2$ gas mixture, and autoclaved.

The MECs were connected in parallel to a programmable power supply (model 3645A; Circuit Specialists Inc.) with a constant applied potential (Vapp) set at 0.25 V, the optimal potential for Feammox-MECs set up determined by 2-electrode cyclic voltammetry analysis (Supplemental material, FIG. S1). Voltage was recorded every hour with a multimeter (model 2750; Keithley Instruments Inc.) across a 10Ω resistor placed between the lead connecting the anode and the positive terminal of the power supply. Current (I) was calculated using Ohm's law (I=V/R), were V is voltage and R the resistance. Data is reported in terms of volumetric current density (Iv=A/m$^3$) which was found by dividing current by the volume of the culture.

Cyclic Voltammetry

Cyclic voltammetry (CV) was conducted on the anode with the cathode as the counter electrode, and a 1 mm thick Ag/AgCl 3.5M KCl reference electrode (model ET072-1 mm, EDaq Inc.) placed between the working and counter electrodes. MECs were cycled using an Ivium potentiostat, using the Ivium software. Three consecutive scans were conducted which ranged from −1 V to +1 V at a rate of 1 mV/second. Only the last 2 scans are shown to avoid overcrowding of the figure. CVs were conducted in duplicates on MEC with live A6 enrichment culture with and without AQDS to determine possible effects of AQDS on the system. CV was also conducted on MEC with dead A6 enrichment culture with AQDS, and on abiotic control MEC with and without AQDS to confirm the effect Feammox bacteria A6.

Feammox-MECs Operating Conditions

Each Feammox-MEC was inoculated with an A6 enrichment or pure culture in Feammox enrichment medium. The medium contained: $NH_4Cl$ 5 mM; $NaHCO_3$ 0.24 mM, $KHCO_3$ 0.71 mM, $KH_2PO_4$ 0.052 mM, $MgSO_4 \cdot 7H_2O$ 0.41 mM, $CaCl_2$ 0.54 mM, vitamin supplement (ATCC®) 0.1 µl/l, and trace element solution; the last one as described in Sawayama (2006). Electron shuttle compound 9,10-anthraquinone-2, 6-disulfonic acid (AQDS) 0.15 mM was included after determining that its addition facilitated electron transfer to the anode. All vials contained resazurin (1 mg/L) as an indicator of anaerobic conditions. The pH of the medium was initially set to 5-5.5 because Feammox bacteria work best at acidic conditions with pH below 6.3.

Various replicas of Feammox-MECs with working Feammox culture were run (n=4 for enrichment culture, and n=2 for pure culture). Two types of controls were set up to confirm that current production and $NH_4^+$ removal were the result of biotic activity: 1) Feammox-MECs with dead A6 culture by autoclaving, and 2) Abiotic Feammox-MECs with enrichment medium only and no microbial inoculum. Furthermore, positive controls with live Feammox A6 enrichment culture were incubated in batch reactors for $NH_4^+$ oxidation rate comparison. The positive controls were placed in MECs assembles which were not connected to a power supply, therefore they did not have functioning electrodes, thus Fe(III) in the form of 2-line ferrihydrite was included in the medium as the electron acceptor. All the MECs with enrichment culture were placed on a mixing plate at 240 rpm, and later the MECS with pure culture were placed on a magnetic plate with a stirrer to avoid noisy readings generated by movement caused by the mixing culture in the shaker. When current production decreased, headspace was flushed with an 80% $N_2$, 20% $CO_2$ gas mixture.

Chemical Analysis

Samples were taken at three different time points of the Feammox-MECs operation. Each time, 1 ml of the supernatant was filtered using a 0.2 µm pore size syringe filter. The filtered solution was used to determine $NH_4^+$ concentrations in a Dionex™ Ion Chromatograph ICS3000, using a CS-16 column with CS-16 guard column, and a CERS 500 (4 mm) suppressor. Iron was analyzed for the control treatments and to determine the small amount of Fe that was transferred with the enrichment culture seed to the MEC. Total Fe was analyzed by adding 100 µl of the MEC or control culture to 4.8 ml of 1 N HCl and 100 µl of 6.25M $NH_2OH$—HCl, then Fe was quantified photometrically using the ferrozine method analysis. Ferrous iron [Fe(II)] was quantified by direct ferrozine method. Paper pH indicator (Ricca Chemical Company®) was used to measure pH before and after the operation period.

DNA Extraction and Microbial Community Composition

Total genomic DNA was extracted from 5 ml of working culture of one Feammox-MEC at the end of each operation period. DNA extraction was done using the FastDNA® spin kit for soil (MP Biomedicals, USA) according to the manufacturer's instructions. Total DNA was eluted in 100 μl of sterile water and its concentrations were measured using Qubit 2.0® (Invitrogen, USA). All DNA samples were preserved at −20° C. until further analysis.

In order to determine the microbial community composition, sequencing and phylogenetic analysis was performed by Novogene (Beijing, China) as follows: From total genomic DNA, the variable region V4 of the 16s rRNA gene was amplified using the primer set 515F/806R (515 F: 5'-GTGCCAGCMGCCGCGGTAA-3'/806R: 5'-GGAC-TACHVGGGTWTCTAAT-3') with a barcode following the method of Caporaso et al (2011). All PCR reactions were carried out with Phusion® High-Fidelity PCR master mix (New England Biolabs). PCR products quantification and qualification were determined by electrophoresis on 2% agarose gel. The resulting amplicons were pooled, purified, quantified. Sequencing libraries were generated using TruSeq® DNA PCR-free sample preparation kit (Illumina, USA) following the manufacturer's protocol and index codes were added. The library quality was assessed on the Qubit@ 2.0 Fluorometer (Thermo Scientific) and Agilent Bioanalyzer 2100 system. Finally, sequencing was performed on an IlluminaHiSeq2500 platform and 250 bp paired-end reads were generated.

Paired-end reads were assembled by using FLASH V.1.2.7. Raw reads were processed according to QIIME V1.7.0 quality controlled process and chimeric sequences were filtered out using the UCHIME algorithm. A total of 31,969 sequences were obtained which were clustered into operational taxonomic units (OTUs) using Uparse V7.0.1001. Sequences with >97% similarity were assigned to the same OTUs. A total of 995 OTUs were produced. A representative sequence for each OTU was screened for taxonomic annotation using the blastn algorithm against the 2016 NCBI's 16s ribosomal RNA sequences for bacteria and archaea at an e-value of $10^5$. A6's 16s rRNA gene sequence was included to NCBI's database for annotation at the family and genus level of the top 100 most abundant OTUs.

Environmental Scanning Electron Microscopy of the MECs' Anode

The graphite plate working as the anode of a MECs containing live A6 and one from the MEC containing dead A6, from the MECs operated for over 1 month, were analyzed using and Environmental scanning electron microscope (Quanta 200 FE-ESEM) at the Imaging and Analysis Center at Princeton University.

Example 2—Feammox Reactor for Degradation of Fluorochemicals

Figure 11:
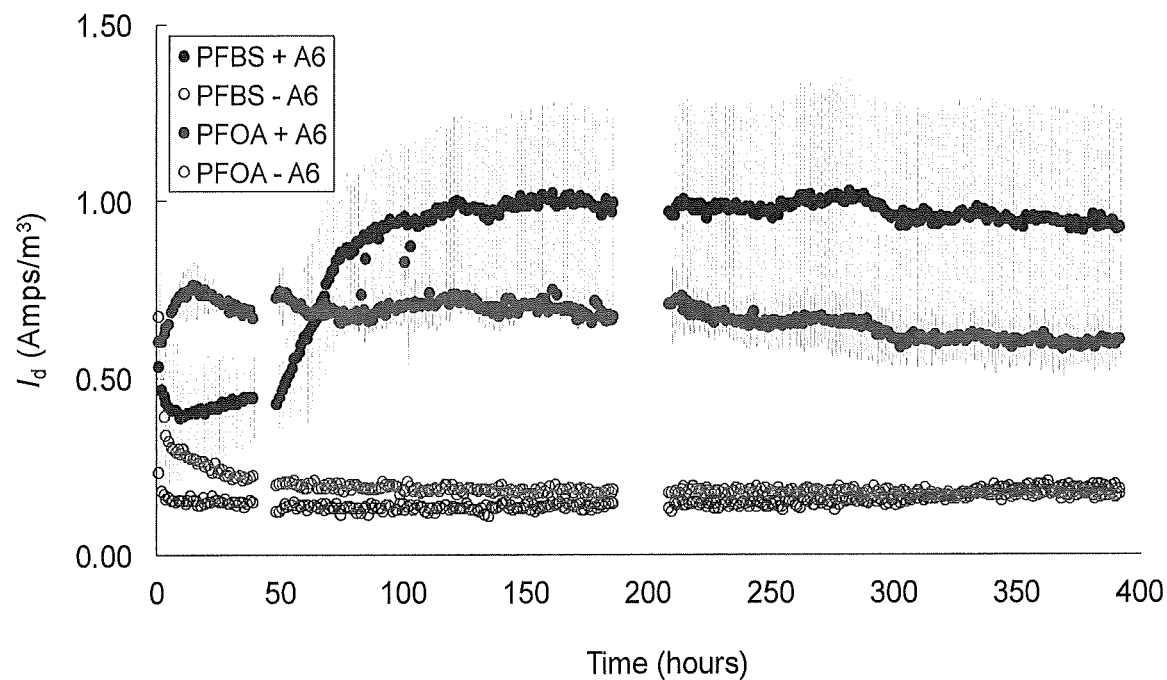
FIG. 11 details current density in a MEC in the presence of PFBS and PFOA (100 mg/l) and a pure A6 culture.
Figure 12:
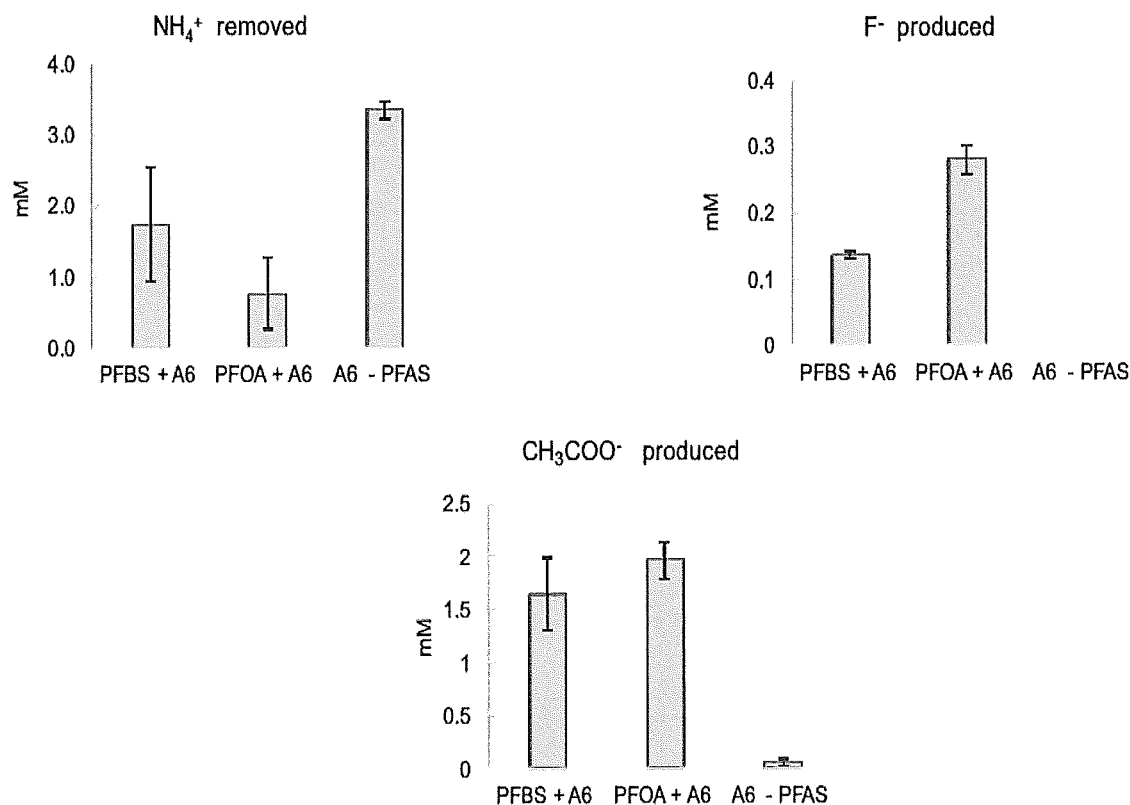
FIG. 12 details $NH_4^+$ removal and F– and acetate production in the presence and absence of PFBS and PFOA.

MECS were constructed and operated as described herein for a period of approximately 2 weeks. Either PFOA or PFBS was added to the MECs to reach a final concentration of 100 mg/l. The MEC's were then seeded with a pure culture of *Acidimicrobiaceae* Feammox bacterium A6 and controls were not seeded. Results presented in FIG. 11 show that, in the presence of A6, a cunent was measured in the MECs with PFOA and PFBS, while in the absence of A6 no current was measured. Results presented in FIG. 12 show that the MECs seeded with A6 removed ammonium over this period, indicating that A6 was active. Over the same period the production of fluoride was observed in the MECs containing PFOA and PFBS. Similarly, the production of acetate was observed. Acetate is a product of the defluorination of perfluorinated substances by A6. The MECs to which no A6 was added did not produce current, did not remove ammonium, nor did they produce fluoride or measurable acetate. These results demonstrate that PFAS (PFOA and PFBS in this case) can be degraded in bioelectrochemical reactors.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

SEQUENCE LISTING

The patent contains a lengthy sequence listing. A copy of the sequence listing is available in electronic form from the USPTO web site (https://seqdata.uspto.gov/?pageRequest=docDetail&DocID=US11807563B2). An electronic copy of the sequence listing will also be available from the USPTO upon request and payment of the fee set forth in 37 CFR 1.19(b)(3).

The invention claimed is:

1. A reactor for ammonium oxidation comprising: a medium including an ammonium component and a Feammox bacterium and/or enzyme(s) thereof capable of oxidizing ammonium coupled with electron transfer to an anode in contact with the medium, wherein the Feammox bacterium colonizes the anode.

2. The reactor of claim 1, wherein the medium does not comprise Fe(III).

3. The reactor of claim 1, wherein the anode comprises metal, alloy or electrically conductive carbon material.

4. The reactor of claim 3, wherein the electrically conductive carbon material comprises graphite.

5. The reactor of claim 1, wherein the electrically conductive carbon material is provided in granular form.

6. The reactor of claim 1 further comprising a cathode.

7. The reactor of claim 6, wherein the cathode is spaced apart from the anode by a separator.

8. The reactor of claim 1, wherein the medium further comprises an electron shuttling compound.

9. The reactor of claim 1 further comprising a power source for application of a potential to the anode.

10. The reactor of claim 1, wherein the medium is aqueous-based.

11. The reactor of claim 1, wherein the medium is wastewater.

12. The reactor of claim 1, wherein the medium is soil.

13. The reactor of claim 1, wherein the medium further comprises one or more contaminants selected from the group consisting of fluorochemicals, chlorinated volatile organic compounds, perchloroethylene (PCE), trichloroethylene (TCE), trichloroethane, dichloroethane, vinyl chloride, polychlorinated biphenyls, fuel constituents, benzene, ethylbenzene, toluene, xylene, phenanthrene, methyl tert butyl ether, tertiary butyl alcohol, polyaromatic hydrocarbons, ethylene dibromide, and inorganic species.

14. The reactor of claim 13, wherein the fluorochemicals comprise perfluoroalkyl compounds, polyfluoroalkyl compounds, fluorinated carboxylic acids, fluorinated alcohols, fluorinated sulfonates or mixtures thereof.

15. The reactor of claim 1, wherein the Feammox bacterium is an Actinobacterium or variant thereof.

16. The claim 15, wherein the Feammox bacterium is an *Acidimicrobiaceae* bacterium or variant thereof.

\* \* \* \* \*